United States Patent [19]

Heinke

[11] Patent Number: 5,429,599
[45] Date of Patent: Jul. 4, 1995

[54] METHOD AND MEANS FOR DELIVERING A PHARMACEUTICAL INTO THE NOSTRIL OF AN ANIMAL

[76] Inventor: Richard M. Heinke, 5120 NW. 38th St., Lincoln, Nebr. 68501

[21] Appl. No.: 236,274
[22] Filed: May 2, 1994
[51] Int. Cl.⁶ .............................. A61M 31/00
[52] U.S. Cl. .................... 604/54; 604/56; 604/192; 604/87; 604/226
[58] Field of Search ............ 128/200.14, 207.18, 128/747; 604/49, 54, 56, 73, 77, 94, 187, 192, 198, 200–202, 218, 244, 82, 87, 226, 231

[56] References Cited

U.S. PATENT DOCUMENTS

| | | | |
|---|---|---|---|
| 2,512,568 | 6/1950 | Saffir | 604/239 |
| 3,506,006 | 4/1970 | Lange | 604/200 X |
| 4,300,545 | 11/1981 | Goodnow et al. | 128/200.14 |
| 4,381,773 | 5/1983 | Goodnow et al. | 604/54 X |
| 5,242,418 | 9/1993 | Weinskin | 604/192 |
| 5,290,254 | 3/1994 | Vaillancourt | 604/192 |
| 5,295,972 | 3/1994 | Mischenko | 604/192 |

*Primary Examiner*—Corrine Maglione
*Attorney, Agent, or Firm*—Zarley, McKee, Thomte, Voorhees & Sease; Dennis L. Thomte

[57] ABSTRACT

A syringe is described which is used in an improved method of vaccinating an animal. The syringe includes a one-piece barrel and needle comprised of a suitable injection molded plastic such as a polycarbonate material with the needle normally being enclosed or shielded by a flexible nasal tip-cap seal. The syringe is filled with a freeze-dried vaccine at the factory and is shipped to the point of use in a sealed pouch. The nasal tip-cap seal is placed in engagement with the cap or cover of a vial containing a diluent such as sterile water. The syringe is moved relative to the vial to cause the needle to pierce through the cover of the vial so that the distal end of the needle is in communication with the interior of the vial. The contents of the vial are then drawn inwardly into the syringe. After the syringe has been removed from the vial, the nasal tip-cap seal again shields the needle and the nasal tip-cap seal is inserted into the nostril of the animal whereupon the vaccine is aspirated into the nostril of the animal.

12 Claims, 2 Drawing Sheets

METHOD AND MEANS FOR DELIVERING A PHARMACEUTICAL INTO THE NOSTRIL OF AN ANIMAL

BACKGROUND OF THE INVENTION

1. Field of the Invention

This invention relates to a method and means for delivering a pharmaceutical, i.e., vaccine, into the nostril of an animal such as a cat, dog, etc., and more particularly to an improved syringe for use in vaccinating such an animal. The syringe could also be used to nasally aspirate a vaccine into the nostril of a human, if so desired.

2. Description of Related Art

Animals such as dogs and cats are frequently vaccinated by injecting the vaccine into one of the nostrils of the animal. For example, see U.S. Pat. No. 4,300,545 which discloses a method and nozzle for nasal vaccination of immature mammals.

A problem associated with the prior syringes and vaccination methods is the large number of steps which are necessary to prepare the syringe, vaccine, etc., for subsequent introduction into the nostril of the animal. Further, it is believed that the prior methods of preparing the syringe for use may result in an improper preparation of the vaccine and possible contamination thereof.

SUMMARY OF THE INVENTION

A method and means for delivering a pharmaceutical such as a vaccine into one of the nostrils of the animal is described. The means for delivering the pharmaceutical into one of the nostrils of the animal comprises a syringe. The syringe could also be used to inject a vaccine into a human, if so desired. The syringe includes an elongated and hollow plastic barrel having an integral plastic needle extending from one end thereof. The barrel and the needle are of one-piece construction and are preferably comprised of a suitable injection molded plastic such as a polycarbonate material. The needle is normally shielded by a nasal tip-cap seal which is secured to one end of the barrel and which extends around the needle. When desired, the nasal tip-cap seal may be deflected or compressed with respect to the barrel to permit the pointed distal end of the needle to pierce through the nasal tip-cap seal.

A hollow piston-plunger is movably received within the barrel of the syringe. An inner piston is slidably received by the interior of the piston-plunger. A freeze-dried, and concentrated vaccine is positioned in one end of the piston-plunger and is maintained therein by the nasal tip-cap seal. When it is desired to deliver the vaccine to one of the nostrils of an animal, the syringe is first positioned against the rubber stopper cap of a vial containing a diluent such as sterile water so that the tip of the nasal tip-cap seal is in engagement therewith. The syringe is then moved with respect to the vial to cause the nasal tip-cap seal to be compressed so that the pointed distal end of the plastic needle pierces through the nasal tip-cap seal and pierces through the rubber stopper cap of the vial. The first piston-plunger is then moved outwardly with respect to the barrel of the syringe to draw the diluent from the vial into the piston-plunger and to mix with the freeze-dried vaccine therein. The syringe is then withdrawn from the vial which permits the nasal tip-cap seal to return to its needle shielding position. The nasal tip-cap seal is then introduced into one of the nostrils of the animal. At that time, the piston-plunger is moved forwardly or inwardly into the barrel to cause the mixed diluent-vaccine to be aspirated through the previously created opening in the nasal tip-cap seal of the syringe and into the nostril of the animal.

It is therefore a principal object of the invention to provide an improved syringe for use in the vaccination of an animal.

Yet another object of the invention is to provide an improved method for vaccinating an animal or a human if so desired.

Yet another object of the invention is to provide an improved method for vaccinating an animal which substantially reduces the steps normally associated with the preparation of the vaccine and the vaccination of the animal.

Still another object of the invention is to provide a method of vaccinating an animal which ensures that the vaccine will not become contaminated during mixing and delivery to the animal.

Still another object of the invention is to provide a method of vaccinating an animal which is convenient.

These and other objects will be apparent to those skilled in the art.

DESCRIPTION OF THE PREFERRED EMBODIMENT

Figure 2:
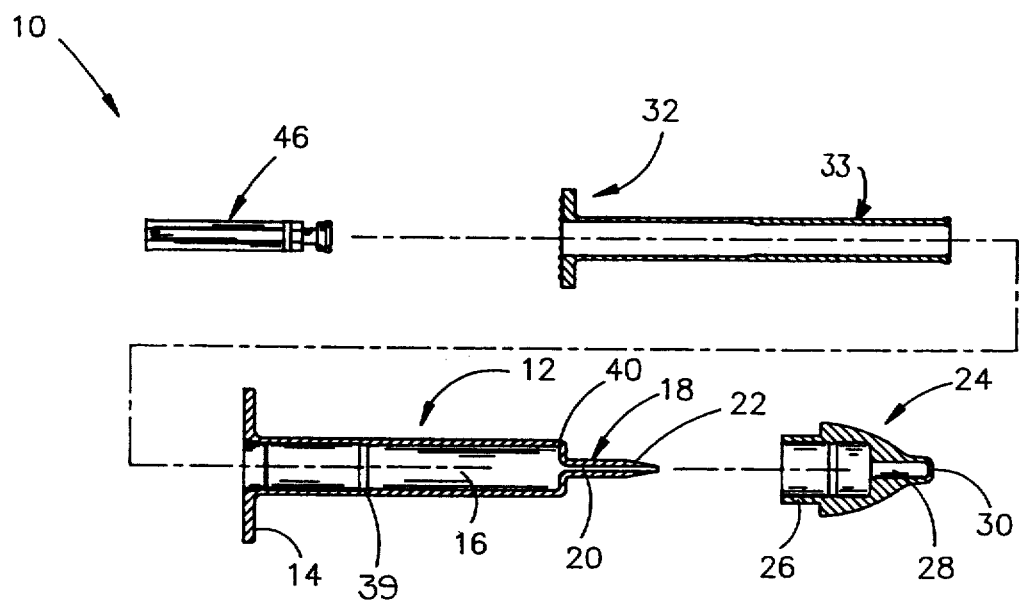
FIG. 2 is an exploded view of the components of the syringe.

The syringe of this invention is referred to generally by the reference numeral 10 and the same would preferably be enclosed in a sealed sterile pouch at the factory. Syringe 10 includes a barrel 12 having a rear opening stop 14, compartment 16 and needle 18 extending from one end thereof. Needle 18 is provided with a bore 20 extending therethrough as best illustrated in FIG. 2. Needle 18 terminates at its distal end in a sharpened or pointed portion 22. Preferably, barrel 12 and needle 18 are of one-piece construction and are preferably comprised of a suitable injection molded plastic such as a polycarbonate material.

Figure 1:
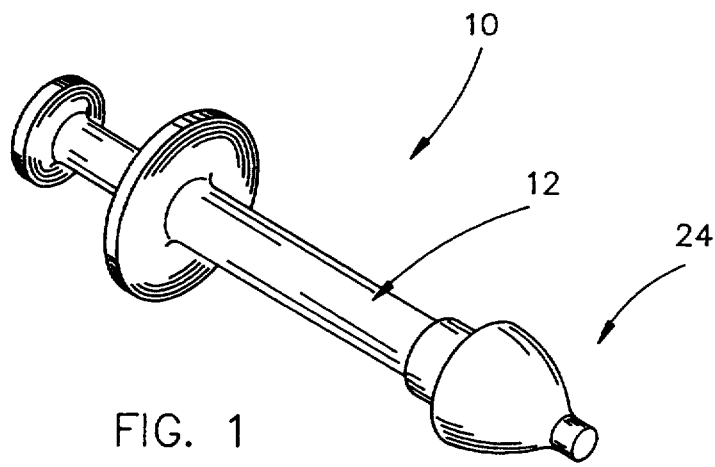
FIG. 1 is a perspective view of the syringe of this invention.

A flexible nasal tip-cap seal 24 is mounted on the end of barrel 12 as illustrated in FIG. 1. Preferably, nasal tip-cap seal 24 is comprised of an injection molded elastomeric plastic material. Nasal tip-cap seal 24 includes a hollow cylindrical portion 26 which embraces the end of barrel 12. Nasal tip-cap seal 24 also includes a cavity 28 which normally receives the distal end of the needle 18. Nasal tip-cap seal 24 also includes a tip portion 30. Nasal tip-cap seal 24 is designed to provide a tapered shut-off type seal of the nostril opening of the animal to facilitate the delivery of the vaccine into one of the nostrils of the animal.

Figure 3:
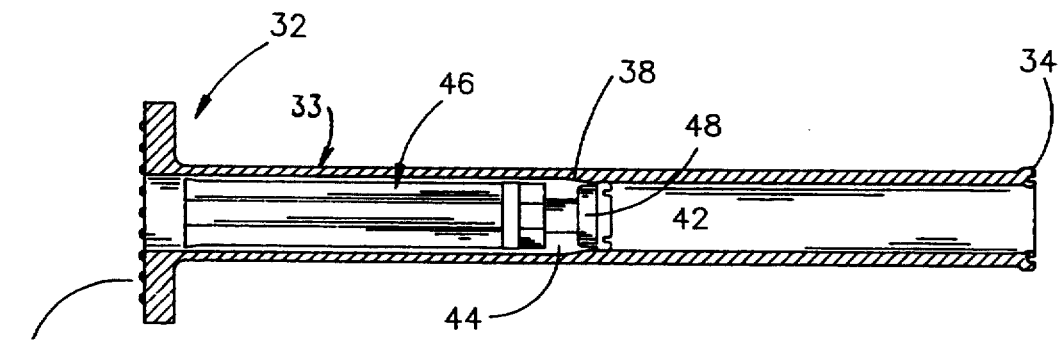
FIG. 3 is a longitudinal sectional view of the piston-plunger and inner piston.

The numeral 32 refers to a piston-plunger assembly including a plunger 33 having an inner end 34 and an outer end 36. Preferably, assembly 32 is comprised of a linear low density polyethylene material. Plunger 33 is hollow as illustrated in FIG. 3 and is provided with a piston stop 38 between the ends thereof as illustrated in FIG. 3. Plunger 33 is selectively slidably received within compartment 16 of barrel 12 and is normally in a position with respect thereto so that the inner end 34 of plunger 33 is adjacent to the shoulder 40 of barrel 12. Plunger 33 may be moved from the position illustrated in FIG. 5 to the position illustrated in FIG. 6 wherein the inner end 34 is positioned adjacent the stop 39 provided in the interior of barrel 12.

For purposes of description, piston stop 38 defines compartment portions 42 and 44 in plunger 33. Piston-plunger assembly 32 also includes an inner piston 46 which is slidably received in plunger 33 as illustrated in FIG. 3 and normally is positioned with respect to the plunger 33 as illustrated in FIG. 3 with the piston 48 being positioned adjacent stop 38. Compartment portion 42 contains a freeze-dried vaccine 50 therein.

Figure 6:
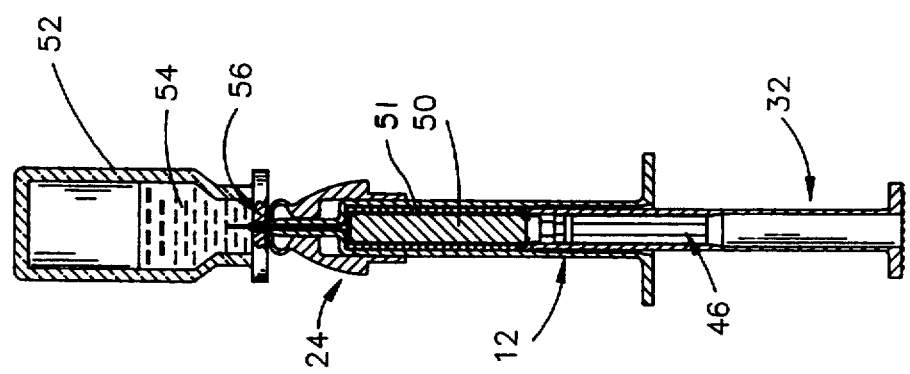
FIG. 6 is a longitudinal sectional view illustrating the syringe drawing diluent from a vial.
Figure 5:
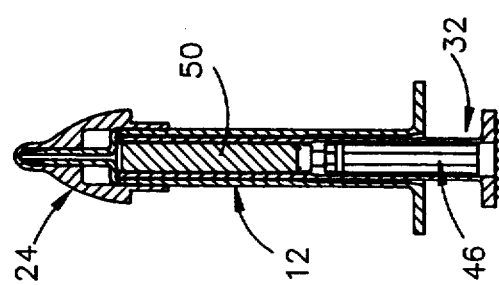
FIG. 5 is a longitudinal sectional view of the assembled syringe.
Figure 4:
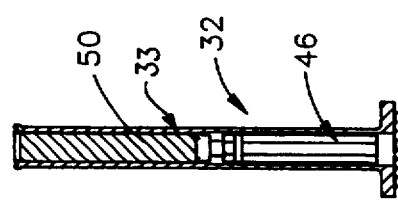
FIG. 4 is a view illustrating the piston-plunger and inner piston together with the freeze-dried vaccine therein.

The syringe 10 is normally assembled at the factory in the manner illustrated in FIG. 5 with the inner end of the plunger 33 being positioned adjacent shoulder 40 of barrel 12 and with the piston 48 of inner piston 46 being positioned adjacent stop 38. The syringe would normally be sealed in a sterile pouch at the factory and would be shipped or transported to the end user. When it is desired to vaccinate an animal, a vial 52 containing a diluent such as sterile water 54 would be utilized. The vial 52 is provided with a rubber stopper cap 56 as illustrated in FIG. 6. The vial 52 is inverted as viewed in FIG. 6 and the tip portion 30 of nasal tip-cap seal 24 is positioned in engagement with the rubber stopper cap 56 as illustrated in FIG. 6. Syringe 10 is then moved upwardly with respect to the vial 52 so that the nasal tip-cap seal 24 is compressed to enable the pointed distal end 22 of needle 18 to pierce through tip portion 30 and to pierce through rubber stopper cap 56 so that the needle 18 is in communication with the interior of the vial 52.

The plunger 33 is then moved downwardly with respect to barrel 12 as illustrated in FIG. 6 to cause a vacuum (difference in pressure) to exist in compartment 42 while simultaneously causing inner piston 46 to remain in place with respect to barrel 12 even though plunger 33 has moved downwardly with respect to inner piston 46. The downward movement of plunger 33, while inner piston 46 remains in place, causes the inner piston 46 to hold the vaccine 50 within barrel 12. In other words, the inner piston 46 pushes the vaccine from compartment 42 into barrel 12 as plunger 33 moves downwardly with respect to barrel 12. Inasmuch as the inner end of plunger 33 no longer surrounds the vaccine 50 when plunger 33 is moved downwardly with respect to barrel 12 as just described, an annular space 51 is created between vaccine 50 and barrel 12.

As plunger 33 is moved downwardly with respect to barrel 12 as described, the diluent from the vial streams downwardly over the vaccine 50 tending to equalize the vacuum. At the same time, as the volume in barrel 12 increases, air bubbles will pass through the annular space 51 and the vaccine to create turbulence through counterflowing diluent thereby mixing the diluent and vaccine in an ideal manner. The passage of the diluent around the vaccine 50 in space 51 ensures that the vaccine and diluent will be thoroughly mixed.

Figure 7:
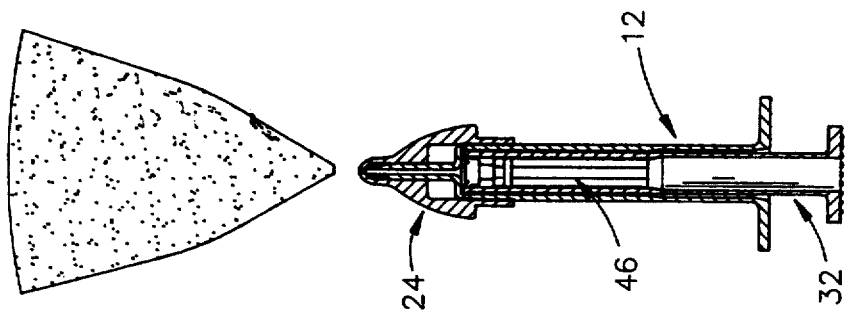
FIG. 7 is a view similar to FIG. 6 except that the syringe is aspirating the vaccine therefrom.

The syringe is then withdrawn from the vial which permits the nasal tip-cap seal 24 to resume its original shape so that the pointed distal end 22 of needle 18 is again shielded as viewed in FIG. 7. The nasal tip-cap seal 24 is then inserted into the nostril of an animal and the piston-plunger assembly 32 is then moved inwardly with respect to barrel 12. The inward or forward movement of the piston-plunger assembly 32 also causes the inner piston 46 to move inwardly or forwardly and the cooperative movement causes the vaccine to be aspirated from the opening previously created in the nasal tip-cap seal 24 by the needle 18. Thus, during the actual aspiration of the vaccine into the nostril of the animal, the needle 18 is shielded to prevent an inadvertent needle stick of the animal.

Thus it can be seen that a novel method and means for vaccinating an animal has been provided which substantially reduces the steps normally associated with such a procedure. It can also be seen that the method and means described herein ensures that the vaccine will not be contaminated. Further, the method and means described herein accomplishes at least all of its stated objectives.

I claim:

1. The method of delivering a pharmaceutical into one of the nostrils of a living creature, comprising the steps of:

(a) providing a syringe including an elongated hollow barrel having a rearward end and forward end and being comprised of a plastic material; said barrel having a rear opening at its rearward end; said barrel having a rear opening stop provided thereon; said barrel having a first compartment provided therein which extends forwardly from said rear opening for receiving a first plunger therein; said barrel having a needle at its forward end, said needle having a rearward proximal end in communication with the forward end of said barrel and a pointed distal end; a flexible tip and cap seal mounted on the forward end of said barrel which normally encloses said needle but which may be deflected rearwardly with respect to said needle to permit said pointed distal end of said needle to pierce therethrough to expose said pointed distal end of said needle; said barrel having a plunger stop provided therein which is positioned forwardly of the rear end thereof; a first elongated and hollow piston-plunger selectively slidably mounted in said first compartment of said barrel; said first piston-plunger having inner and outer ends; said first piston-plunger being selectively movable from a first position wherein its said inner end is positioned adjacent said forward end of said barrel to a second position wherein said inner end is positioned adjacent said plunger stop of said barrel; said first piston-plunger having a piston stop provided therein between the ends thereof; an inner piston slidably mounted in said first piston-plunger and having inner and outer ends; said inner piston being movable from a first position wherein its said inner end is positioned adjacent said piston stop of said first piston-plunger to a second position wherein said inner end is positioned adjacent to said inner end of said first piston-plunger; said inner piston normally being in said first position; said first piston-plunger normally being in said first position;

(b) placing a freeze-dried vaccine in said first piston-plunger between said inner end and said piston stop;

(c) providing a vial which has a diluent therein and which is maintained therein by a cap means on the upper end thereof;

(d) inverting said vial;

(e) positioning said syringe so that said flexible tip-cap seal is in engagement with said cap means of said vial;

(f) moving said syringe upwardly with respect to said vial to cause said pointed end of said needle to pierce through said flexible tip-cap seal and to pierce through said cap means of said vial;

(g) moving said first piston-plunger to its said second position to withdraw the diluent from said vial into said first piston-plunger and to come into contact with the freeze-dried vaccine therein;

(h) removing said syringe from said vial;

(i) positioning said flexible tip-cap seal in the nostril of the living creature; and (j) moving said first piston-plunger to its said first position while moving said inner piston to its said second position to aspirate the vaccine-diluent mixture into the nasal passage of the living creature.

2. The method of claim 1 wherein said diluent is mixed with said vaccine as said diluent is drawn into said first piston-plunger.

3. The method of claim 1 further including the step of shielding said pointed distal end of said needle during the aspiration of the diluent-vaccine mixture into the nostril of the living creature.

4. The method of claim 1 wherein step (g) includes the mixing of the diluent and the vaccine by creating turbulence in the diluent as it is brought into contact with the vaccine.

5. The method of claim 1 wherein step (g) includes the mixing of the diluent and the vaccine by creating air bubbles in the diluent as it is brought into contact with the vaccine.

6. A syringe, comprising:

an elongated hollow barrel having a rearward end and a forward end and being comprised of a plastic material;

said barrel having a rear opening at its rearward end;

said barrel having a rear opening stop provided thereon;

said barrel having a first compartment provided therein which extends forwardly from said rear opening for receiving a first plunger therein;

said barrel having a hollow needle at its forward end, said needle having a rearward proximal end in communication with the forward end of said barrel and a pointed distal end;

a flexible tip and cap seal mounted on the forward end of said barrel which normally encloses said needle but which may be deflected rearwardly with respect to said needle to permit said pointed distal end of said needle to pierce therethrough to expose said pointed distal end of said needle;

said barrel having a plunger stop provided therein which is positioned forwardly of the rearward end thereof;

a first elongated and hollow piston-plunger selectively slidably mounted in said first compartment of said barrel;

said first piston-plunger having inner and outer ends;

said first piston-plunger being selectively movable from a first position wherein its said inner end is positioned adjacent said forward end of said barrel to a second position wherein said inner end is positioned adjacent said plunger stop of said barrel;

said first piston-plunger having a piston stop provided therein between the ends thereof;

an inner piston slidably mounted in said first piston-plunger and having inner and outer ends;

said inner piston being movable from a first position wherein its said inner end is positioned adjacent said piston stop of said first piston-plunger to a second position wherein said inner end is positioned adjacent said inner end of said first piston-plunger;

said inner piston normally being in said first position;

said first piston-plunger normally being in said first position.

7. The syringe of claim 6 wherein said barrel, said tip and cap seal, and said piston plunger are comprised of a plastic material.

8. The syringe of claim 7 wherein said barrel and said needle are of one-piece construction.

9. The syringe of claim 8 wherein said barrel and said needle are comprised of an injection molded plastic.

10. The syringe of claim 9 wherein said injection molded plastic is a polycarbonate material.

11. The syringe of claim 6 wherein said barrel and said needle are comprised of an injection molded plastic.

12. The syringe of claim 11 wherein said injection molded plastic is a polycarbonate material.

* * * * *